March 7, 1967 B. Y. KAMADA Plant Pat. 2,723
POMEGRANATE TREE
Filed Dec. 10, 1965
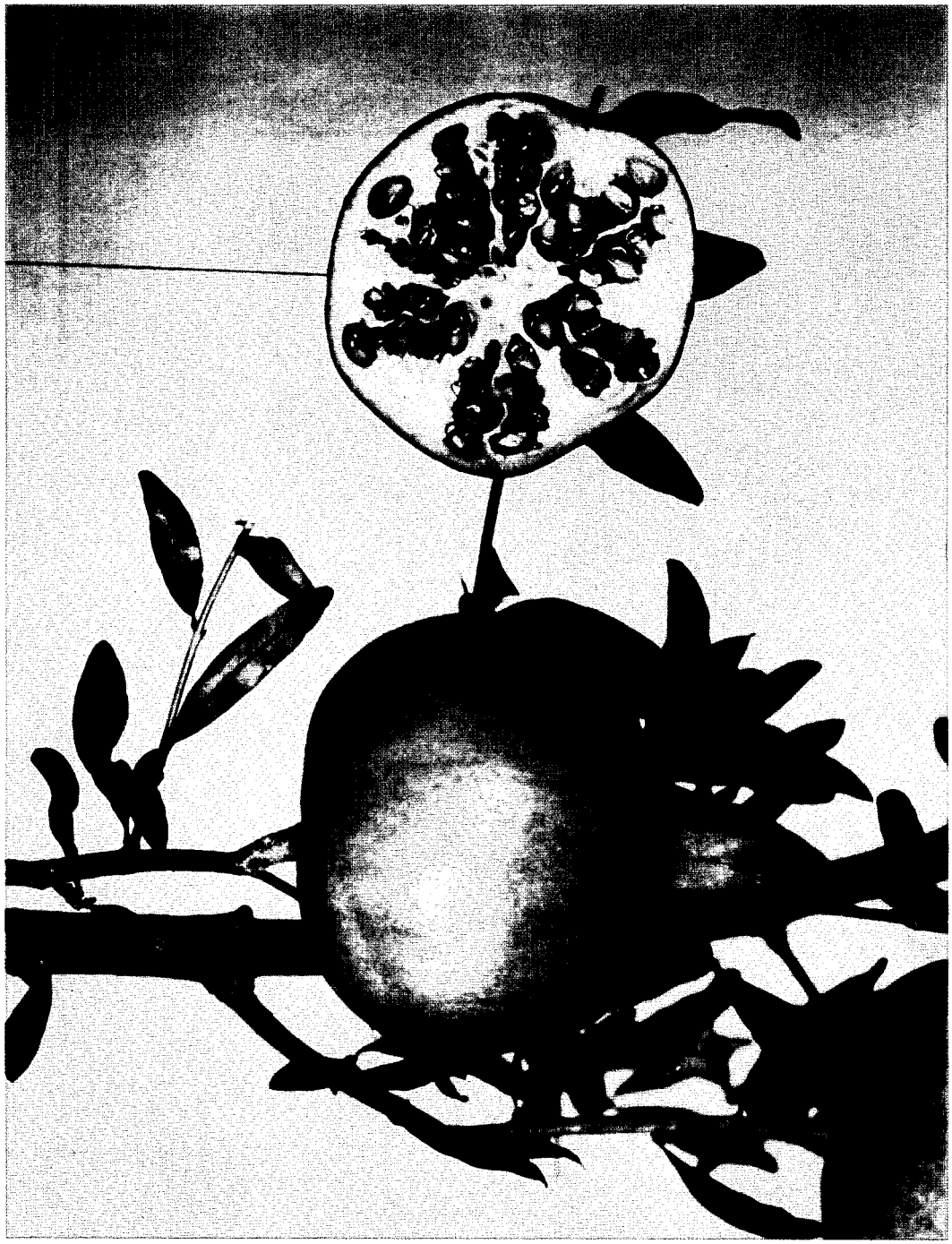
BENJAMIN Y. KAMADA
INVENTOR
Huebner & Worrel
ATTORNEYS United States Patent Office Plant Pat. 2,723
Patented Mar. 7, 1967

2,723
POMEGRANATE TREE
Benjamin Y. Kamada, 24627 E. Adams,
Orange Cove, Calif. 93646
Filed Dec. 10, 1965, Ser. No. 512,835
1 Claim. (Cl. Plt.—33)

The present invention relates to a promegranate tree and more particularly to a new and distinct variety thereof broadly characterized by its vigorous growth and regular bearing of early-maturing, brightly colored, uniformly round, pomegranates having an abundance of tender, sweetly flavored seed arils and a relatively thin rind which resists splitting.

The instant variety pomegranate tree blooms at about the same time as the Wonderful pomegranate tree (unpatented) which the instant variety most nearly resembles. Its fruit, however, distinguishes from the fruit of the Wonderful in that it matures about three weeks earlier at which time it has a ratio of only about .7% acid to the total soluble solids of the fruit which is well below the 1.85% acidity required for harvest. The fruit of the instant variety further distinguishes over the fruit of the Wonderful in its more brightly dark red colored rind surface and its more attractively uniformly round form.

I discovered the instant variety of pomegranate tree as a sport growing on a Wonderful pomegranate tree in an orchard of such trees on my ranch at 24627 East Adams Avenue near Orange Cove, Fresno County, California. I asexually reproduced it by cuttings made from the original sport. The trees resulting from said cuttings fruited and the fruit and tree characteristics proved identical to those of the original sport.

The accompanying drawing is a color photograph of a representative branch and two mature fruit of the instant variety with one divided in a plane taken generally along its major axis to reveal flesh coloration and the edible seed aril thereof.

Referring more specifically to the pomological details of this new and distinct variety of pomegranate tree, the following has been observed under the ecological conditions prevailing at the designated orchard at Orange Cove, California, and is an outlined description thereof. All major color plate identifications are by reference to the Nickerson Color Fan of the American Horticultural Council.

*Tree*

Size: Small, round, compact, and bushy; usually deciduous.

Trunk: Knotty, irregular, suckering freely from roots and crown.

Branches: Slender, twiggy, nearly cylindrical, somewhat thorny; new growth four-angled, with thorns being of modified stem structure and not of leaf origin. Thorns average ¼" to ¾", in length.

Leaves:
- *Size.*—Medium.
- *Length.*—Averaging 3".
- *Width.*—Averaging ½".
- *Form.*—Lanceloate, long or obovate, obtuse, entire, glabrous, red-veined during early growth.
- *Color.*—Moderate olive green (5GY 4/3) to grayish-olive green (5GY 3/2).
- *Margin.*—Without glands and marginal veins.
- *Petiole.*—Medium short, medium thick.
- *Stipules.*—Few at base of leaf.

Flowers: Profuse, large, axiallary; solitary or in small clusters; borne mainly at the tips of the branches in the mantle of the tree.

Size: Averaging 1¼".

Calyx: Stiff, tubular, showy; reddish-orange in color, five to seven lobes or sepals, crowned with crumpled petals; bright scarlet and white in color; lanceolate to ovolate in form; equal in number to the sepals and inserted between them.

Stamens: Numerous, inserted on inner wall of calyx tube.

Ovary: Inferior, spherical, imbedded in fleshly calyx tube or receptacle, surmounted by single long, slender style; contains seven to fifteen carpels or locules arranged in two whorls or series, one interior and lower, containing three carpels; the other exterior and upper, containing six to twelve carpels.

Stigma: Small, discoid.

*Fruit*

Maturity when described, firm ripe.

Size: Medium. Axial diameter, averaging 3½" under normal environmental and horiticultural conditions with usual thinning to space fruit along the fruit-bearing branches. Transverse in a plane common with the major axis, averaging 3½". At right angle to major axis, averaging 2¾".

Form: Generally round, obovate, slightly flattened at base and apex.
- *Calyx tube.*—Medium to short, lobes reflexed.
- *Rind.*—Thin, tough, resists splitting. Color—bright dark red (5R 3/7).
- *Flesh.*—Abundant, small amount of rag or pulp; astringent, bitter. Color—Brilliant yellow (5Y 9/9).
- *Seeds.*—Small in proportion to the aril, fairly tender and easily eaten.
- *Aril.*—Succulent, juice abundant, rich flavor, sprightly, vinous and subacid extended to the rind. Color—transparent, dark red (5R 3/7).

Use: Fresh market, local and distant, culinary.
- *Keeping quality.*—Excellent.
- *Shipping quality.*—Excellent.

Although the new variety of pomegranate tree possesses the described characteristics of the growing conditions in Fresno County, California, in the central portion of the San Joaquin Valley, it is to be understood that fluctuations of the usual magnitude in characteristics incident to growing conditions, fertilizaton, pruning and pest control are to be expected.

Having thus described and illustrated my new variety of pomegranate tree, what is claimed as new and desired to be secured by Letters Patent is:

A new and distinct variety of pomegranate tree substantially as illustrated and described and which is characterized by its vigorous growth and its regular and heavy bearing of early-maturing fruit which ripen about three weeks earlier than the fruit of the Wonderful pomegranate tree (unpatented), which the new variety most nearly resembles, but from which it is distinguished by its fruit providing a lower ratio of acid to the total soluble solids of the fruit at such early date of maturity and by its fruit being more uniformly roundly formed and having a thinner, more brightly dark red colored rind surface which has a greater resistance to splitting.

No references cited.

ABRAHAM G. STONE, *Primary Examiner.*

ROBERT E. BAGWILL, *Examiner.*